United States Patent [19]

Palfray

[11] Patent Number: 4,536,898
[45] Date of Patent: Aug. 27, 1985

[54] DEVICE FOR THE ALIGNMENT RESEARCH, ALIGNMENT AND ORIENTATION OF PROSTHESIS OF THE LOWER LIMBS

[75] Inventor: Michel R. Palfray, Seurre, France

[73] Assignee: Etablissements Proteor, Dijon, France

[21] Appl. No.: 473,134

[22] Filed: Mar. 7, 1983

[30] Foreign Application Priority Data

Jul. 30, 1982 [FR] France .................................. 82 13332

[51] Int. Cl.$^3$ .............................................. A61F 1/02
[52] U.S. Cl. ........................................ 623/33; 623/38; 623/27
[58] Field of Search ..................... 3/21, 20, 19, 18, 17, 3/17 SS

[56] References Cited

U.S. PATENT DOCUMENTS 2,877,506  3/1959  Almoslino ......................... 273/1 SS
3,538,516  11/1970  Bailey et al. ............................. 3/21

Primary Examiner—Richard J. Apley
Assistant Examiner—David J. Isabella
Attorney, Agent, or Firm—Browdy and Neimark

[57] ABSTRACT

The device for the alignment research, the alignment and orientation of a first portion of a prosthesis with respect to second portion of said prosthesis comprises at least three elements, two of said elements having spherical contact surfaces and two of said elements having flat contact surfaces, said elements being interposed between said first and second portions of prosthesis and moved one with respect to the other to adjust the respective positioning and orientation of said two portions of prosthesis.

12 Claims, 10 Drawing Figures

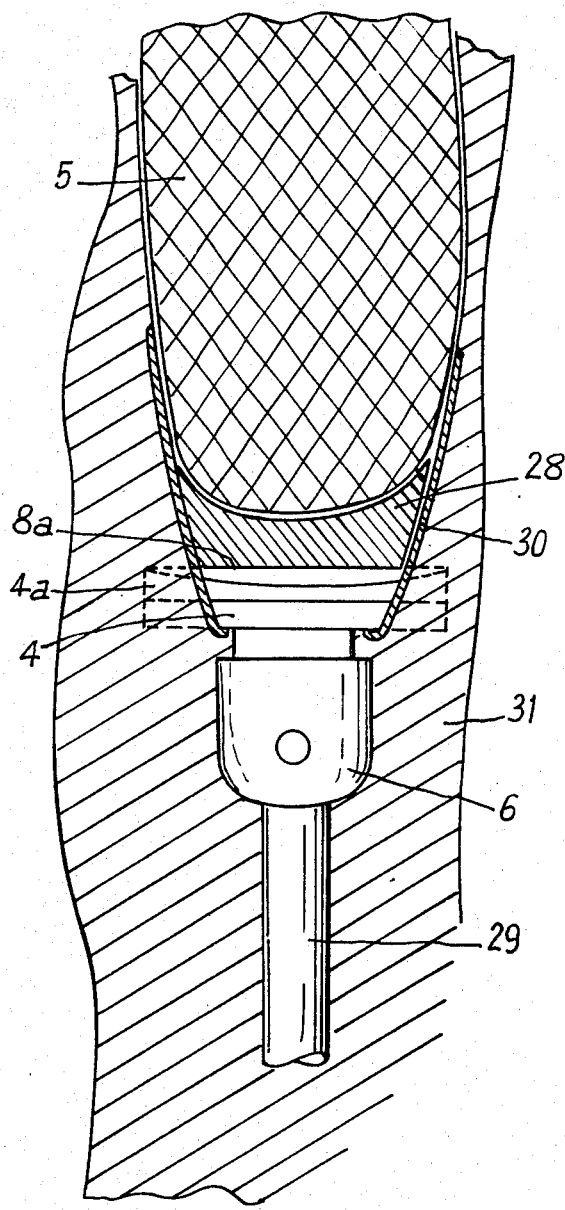
Fig: 7
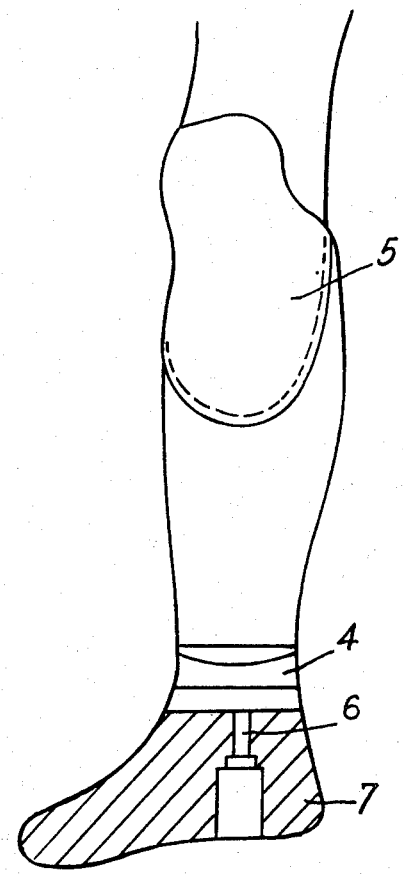
Fig: 8

DEVICE FOR THE ALIGNMENT RESEARCH, ALIGNMENT AND ORIENTATION OF PROSTHESIS OF THE LOWER LIMBS

BACKGROUND OF THE INVENTION

The present invention relates to a new device for the alignment research, alignment and orientation of prosthesis of the lower limbs.

The device of the invention is provided for alignment and/or orientation adjustments of a portion of a prosthesis with respect to the others, for example of the juncture of a prosthesis for amputation of a thigh or of a leg, in order to obtain the best static and dynamic positions when the patient is walking.

In addition, the device of the invention can be manufactured at a low cost and extremely simply and is of a light weight. Moreover, the device of the invention, once set in position, can be completely imbedded into a shape simulating the outer aspect of the amputated limb.

SUMMARY OF THE INVENTION

According to the invention, the device for the alignment research, alignment and orientation of a prosthesis with respect to a stump of an amputated limb comprises at least three elements stacked upon each other, the end elements being fixed between two portions of the prosthesis, a mounting mode being to fix one of them to a juncture and the other to another prosthesis portion, the surface in contact of at least two of said elements being a spherical surface portion, and means being provided for maintaining together said elements during their mutual and relative displacement in two perpendicular planes in order to modify, on the one hand, the just stand or poise and, on the other hand, the orientation of the stump of the amputated person to whom the prosthesis is adapted.

Various other features of the invention will become more apparent from the following detailed description.

BRIEF DESCRIPTION OF THE DRAWINGS

Embodiments of the object of the invention are shown by way of non limiting examples in the accompanying drawings, in which:

FIG. 7 is an elevation view showing the device when applied to a prosthesis of the thigh;

FIG. 8 is a diagrammatic elevation view showing application of the device to a prosthesis of the leg;

DESCRIPTION OF A PREFERRED EMBODIMENT

Figure 1:
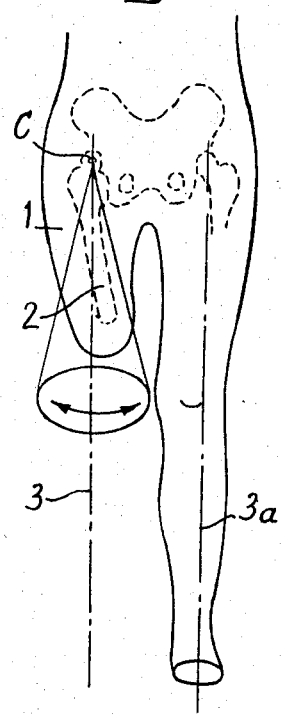
FIG. 1 is a front diagrammatic elevation view of a person with his or her leg amputated at the thigh.

FIG. 1 is a front view of a person with his right leg amputated at the thigh, reference 1 designating the stump and reference 2 the femur segment, both the stump and the femur having a deviation with respect to the vertical line shown at 3 as regards the stump, and at 3a as regards the sound leg.

Figure 2:
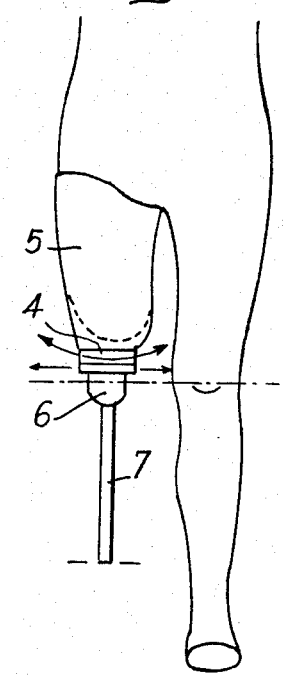
FIG. 2 is a similar view to FIG. 1, diagrammatically showing the alignment device of the invention.

In order to provide the amputated person with an appropriate artificial limb, the invention provides an alignment research, alignment and orientation device designated generally at 4. The device 4 is fixed at the lower portion of the juncture 5 which can be the thigh, as shown in FIGS. 2 and 7, or the leg as shown in FIG. 8, or any other portion of the prosthesis. On the other hand, the device 4 is connected to a mechanism 6 which is part of the prosthesis 7, the mechanism 6 being a knee or foot articulation as shown in FIGS. 2, 7 and 8, or another portion of the prosthesis.

Figure 3:
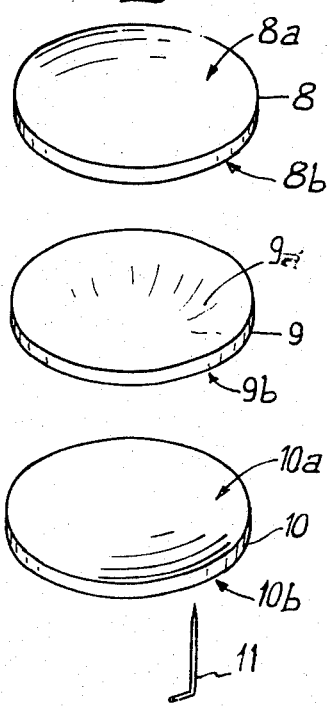
FIG. 3 is an exploded perspective view of the device of the invention, according to a first embodiment.

FIG. 3 shows a first embodiment of the device 4 which comprises three elements 8, 9 and 10. The element 8 has a top portion 8a adapted for being connected to a prosthesis portion, and a convex bottom 8b. The disc 9 has a concave top portion 9a of same radius of curvature as the convex bottom portion 8b of the element 8. The bottom portion 9b of the element 9 is plane, as well as the top portion 10a of the element 10, the bottom portion 10b of which is adapted for being connected for example to the mechanism 6 or to any other portion of the prosthesis.

The centre of the radius of curvature of the convex surface of the element 8 and of the concave surface of the element 9 is adjacent the articular centre of the overlying articulation C of the prosthesis or of the amputated person.

By displacing the element 9 with respect to the element 8, it is possible to set the angle of the stump with respect to the vertical line 3, both in the frontal plane and in the sagittal plane, and also in all the intermediate planes. On the other hand, the displacement of the plane face 10a of the element 10 against the plane face 9b of the element 9 provides for the displacement of the load line with respect to the frontal plane as well as to the sagittal plane in order to take in account the particular morphology of the patient to be fitted with the prosthesis and therefore to provide the alignment of said prosthesis.

The hereabove described elements with reference to FIG. 3 are advantageously made of a material as light in weight as possible and, preferably, of a plastics material loaded with a magnetized material, for example a rubber impregnated with magnetized ferrite. This arrangement enables to carry out the necessary settings, then the elements are locked together, for example through a pin such as that shown at 11 in FIG. 3. A rectifying of the periphery of the elements displaced with respect to each other can also be carried out so that their outer generating lines be in alignment with those of the juncture 5 and of the prosthesis. Thereafter, the whole device can be imbedded in a resin or surrounded, as well at least as the bottom of the juncture and the top of the prosthesis, with adhesive bands in order to provide a final immobilization.

Figure 4:
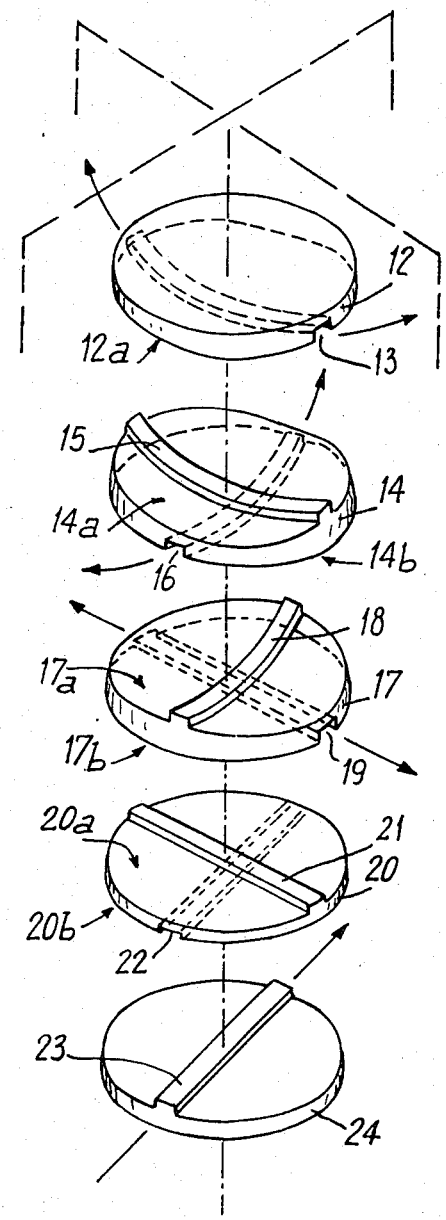
FIG. 4 is an exploded perspective view of the device of the invention, according to a second embodiment.

FIG. 4 shows an alternative embodiment enabling a fabrication of the device from any desired material, for example from plastics material. In this alternative embodiment, the device comprises: a first element 12 the lower face 12a of which is convex and in which is formed a slot 13, a second element 14 the top portion 14a of which is concave and is formed with a rib 15 sliding in the slot 13, the bottom portion 14b of the element 14 being itself convex and formed with a slot 16 which is orthogonal with respect to the rib 15 engaged inside the slot 13 of the element 12. A third element 17 has, as the element 14, a concave top portion 17a and a rib 18 corresponding to the slot 16 of the element 14. The bottom of the element 17 is plane and formed with a slot 19 orthogonal to the rib 18. A fourth element 20 of which the top and bottom portions 20a, 20b are plane, is formed on its top with a rib 21 corresponding to the slot 19 of the element 17 and on its bottom portion with a slot 22 co-acting with a rib 23 formed in a fifth element 24 the top of which is plane.

As results from the foregoing, displacement of the element 24 with respect to the element 20 can be achieved in a plane, while the displacement of the element 20 with respect to the element 17 can be achieved in a perpendicular plane. The corresponding ribs and slots of the various elements being orthogonal, all the poise settings can be carried out as a function of the morphology of the amputated person to be fitted with a prosthesis.

On the other hand, the relative displacement which can be imparted to the element 17 relative to the element 14, and to the element 14 relative to the element 12 enables due to the relative position of their ribs and slots to carry out all the necessary orientation settings.

The described embodiment permits the manufacture by casting or machining or any other mode authorized by the techniques relating to parts made of wood, plastics, or any other suitable material, and the fixation of the part together can be provided by gluing, fitting with a pin, or any other means known in the art.

Figure 5:
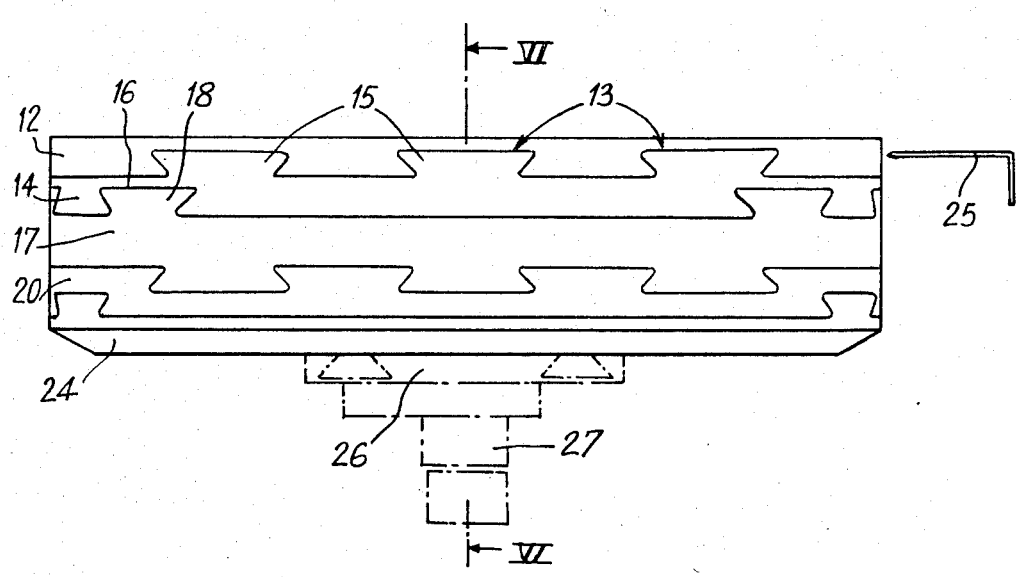
FIG. 5 is an enlarged front elevation view showing the device according to a preferred embodiment.
Figure 6:
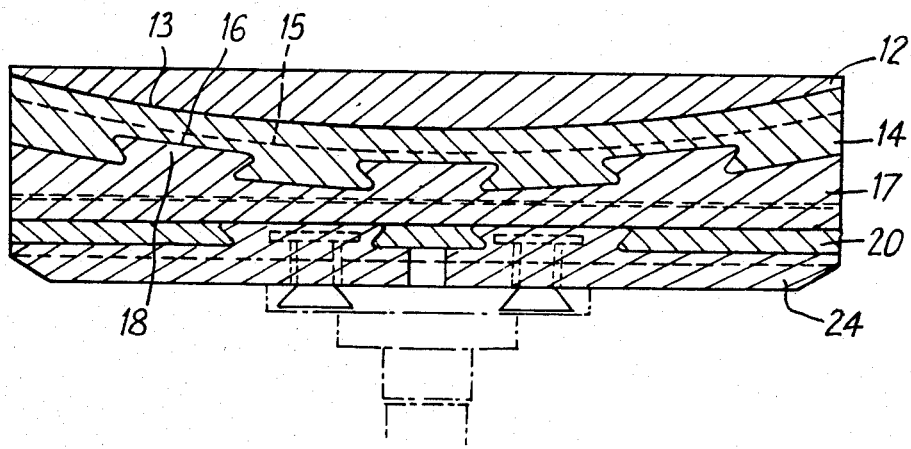
FIG. 6 is a sectional view along line VI—VI of FIG. 5.

FIGS. 5 and 6 show a development of the embodiment of FIG. 4, according which the elements 12, 14, 17, 20 and 24 are each formed with slots 13, ribs 15, slots 16, ribs 18, etc . . . , in the shape of dovetails and alternated, so that the successive elements are guided in two perpendicular planes by the dovetailed assembly unit.

While the prosthesist proceeds to intermediate adjustment settings, the various elements can be immobilized relative to each other by means of pins 25, screws or any appropriate means, and this until the final setting is obtained.

For an embodiment concerning a prosthesis of the thigh, the top of the first element 8 or 12 if first fixed provisionally, for example by gluing to the base 28 of the juncture 5, then the last element 24 is also fixed provisionally on the connection 26 of an element 6, for example by screwing, and then one proceeds to the adjustment settings as hereabove described. Following that, the peripherical edge of the device 4 is machined in order to adjust the periphery 4a which is protruding relative to the base 28 of the juncture.

Then, the elements are blocked and definitely fixed to the juncture 5. An embodiment consists in wrapping, around the juncture 5, bands 30 impregnated with a plastics material in order to form a stratification forming a connection between the juncture and the device 4. Finally, a stuffing 31 is put in place in a manner known per se in order to surround the whole framework of the prosthesis and the device, and form the silhouette of a thigh, a knee and a natural leg.

In the foregoing, the concave or convex surfaces are indifferently of spherical or cylindrical generating lines.

FIG. 8 shows an application of the device for the prosthesis of a leg; in this case, the device is mounted immediately above the foot. As previously and after the setting, the periphery of the device is modified so as to be adapted exactly to the outer shape which the prosthesis has to present.

Figure 9:
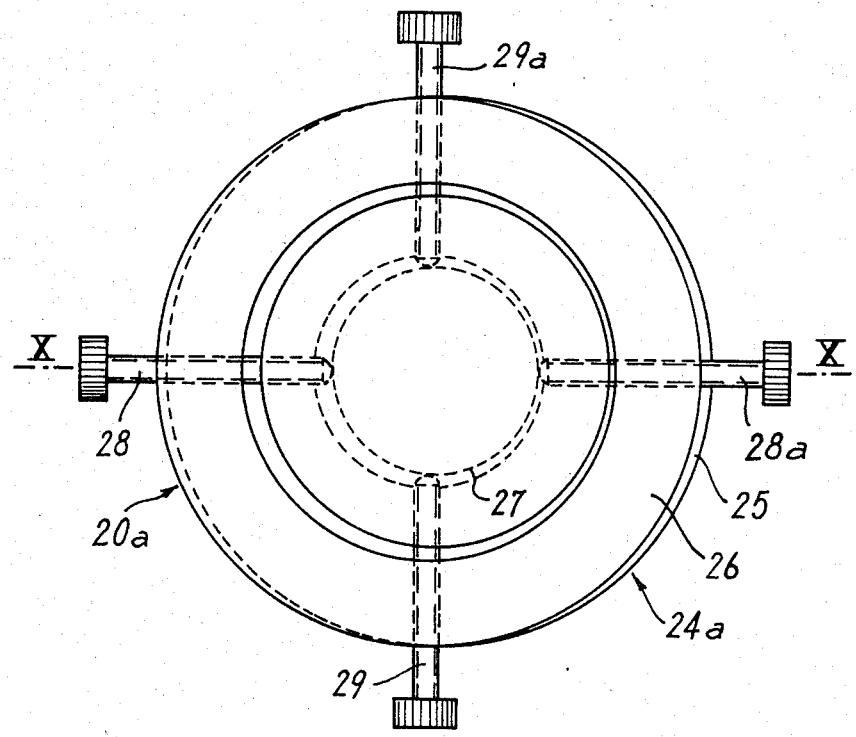
FIG. 9 is a diagrammatic plan view from above of a simplified alternative embodiment of the device.
Figure 10:
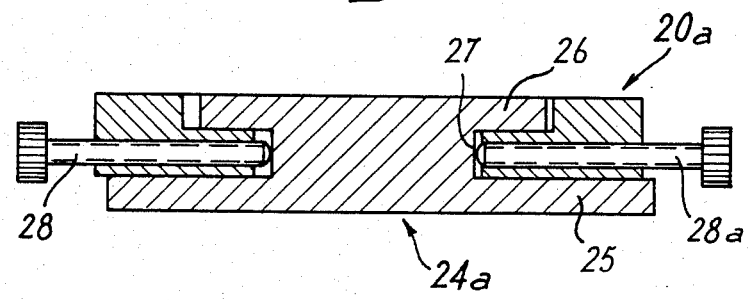
FIG. 10 is a cross-sectional view taken along line X—X of FIG. 9.

FIGS. 9 and 10 show an alternative embodiment of a simplified device providing for the alignment of the prosthesis, independently of the orientation of the prosthesis, when such an orientation is not necessary or provided by a means other than those hereabove discussed. The alternative embodiment of FIGS. 9 and 10 plays the parts of the elements 20 and 24 of FIG. 4. In other words, an element 24a is made of two concentrical discs 25, 26 superimposed and connected together by a hub 27 around which is mounted an element 20a which is ring-shaped and in which are disposed two sets of pins or screws 28, 28a and 29, 29a, respectively offset by 90°. In this alternative embodiment, the element 20a is rigidly connected to the juncture 5 and the element 24a is rigidly connected to the prosthesis 6, 7. By acting on screws 28, 28a, it is possible to displace the elements 20a and 24a respectively, one relative to the other and in a first direction, then to immobilize these two elements in the chosen position. By acting thereafter on screws 29, 29a, the elements 20a and 24a respectively are displaced and then immobilized in a second direction which is offset substantially by 90° relative to the first direction. The accurate and final alignment is then obtaining by acting again on the screws 28, 28a, on the one hand, and 29, 29a, on the other hand. When the correct alignment is established, the elements 20a and 24a are rectified and fixed as explained hereabove in order to be integral with the prosthesis.

The invention is not limited to the embodiments shown and described in detail and various modifications can be carried out without departing from its scope, as shown in the appended claims.

I claim:

1. An adjustment setting device for alignment and angular orientation of a prosthetic device for a lower limb, the prosthetic device including an upper portion and a lower portion, said adjustment setting device comprising:

first adjustment means, connected to said upper portion and having a lower spherical surface;

second adjustment means, connected to said lower portion, and having an upper planar surface;

third adjustment means positioned between, and coacting with, said first and second adjustment means, said third adjustment means including an upper spherical surface and a lower planar surface;

the lower spherical surface of said first adjustment means and the upper spherical surface of said third adjustment means being relatively displaceable in three orthogonal planes to define means for angularly orienting said lower portion relative to said upper portion, the upper planar surface of said second adjustment means and the lower planar surface of said third adjustment means being relatively displaceable in two orthogonal planes to define means for aligning said lower portion relative to said upper portion in any direction in the plane of coaction of the planar surfaces and means for immobilizing said orienting means after said angular orientation has been set, whereby upon first setting said angular orientation of sad prosthesis upper and lower portions, alignment of said upper and lower prosthesis portions in orthogonal horizontal planes may be accomplished without a corresponding simultaneous change in position of the upper and lower portions in a third, vertical plane.

2. The adjustment setting device of claim 1, and further comprising first means for securing said first adjustment means to said third adjustment means, and second means for securing said second adjustment means to said third adjustment means, after alignment and angular orientation of said lower portion relative to said upper portion has been accomplished.

3. The adjustment setting device of claim 1, wherein said third adjustment means consists of first and second elements,
said first element having a concave top surface and a convex bottom surface,
said second element having a concave top surface and a bottom surface defining said lower planar surface,
said bottom surface of said first element and said top surface of said second element both including means for constraining movement of said first and second elements relative to one another in a first plane.

4. The adjustment setting device of claim 3, wherein said adjustment means consists of first and second elements each having top planar faces, said adjustment means first element further having a planar bottom face,
said bottom face of said second adjustment means first element and said top face of said second adjustment means second element including means for guiding movement of said elements relative to one another in said first plane.

5. The adjustment setting device of claim 4, wherein said first adjustment means consists of one element having a top surface fixed to the lower end of said upper portion and a convex bottom surface defining said lower spherical surface,
said first adjustment means bottom surface and said third adjustment means first element top surface both including means for constraining movement of said first adjustment means relative to said third adjustment means in a plane perpendicular to said first plane.

6. The adjustment setting device of claim 5, wherein said constraining means comprises interfitting rib means and slot means.

7. The adjustment setting device of claim 4, wherein said guiding means comprises interfitting rib means and slot means.

8. A device according to claim 1, wherein said first, second and third adjustment means are connected by magnetic means.

9. A device according to claim 3, wherein the radius of curvature of the concave and convex faces has a length corresponding approximately to the distance between said faces and the overlying articular centre (C) of the prosthesis or of the patient.

10. A device according to claim 3, wherein the concave and convex faces are portions of cylindrical surfaces.

11. A method for relative alignment of two portions of a lower limb prosthesis using an alignment setting means comprising co-acting planar adjustment surfaces and an angular orientation means comprising co-acting spherical surfaces, said method comprising the steps of:
positioning said alignment setting means between said two portions, adjusting said alignment setting means by moving the two portions relative to one another in at least one of two orthogonal planes and immobilizing said alignment setting means after having been adjusted in order that they become fixed to the prosthesis, and
positioning said orientation setting means between said two portions for setting orientation of one of the portions relative to the other, adjusting said orientation setting means by moving the two portions relative to one another in at least one of three orthogonal planes and immobilizing said orientation setting means after having been adjusted in order to fix them to the prosthesis,
the step of positioning said orientation setting means occuring after said alignment setting means has been immobilized.

12. A method for relative alignment of two portions of a prosthesis of a lower limb according to either claim 11, comprising the further step of rectifying outer generating lines of the setting means after their immobilization and wrapping the setting means so that they become integral with one at least of the portions of the prosthesis.

* * * * *

UNITED STATES PATENT AND TRADEMARK OFFICE
CERTIFICATE OF CORRECTION

PATENT NO. : 4,536,898

DATED : August 27, 1985

INVENTOR(S) : Michel R. Palfray

It is certified that error appears in the above-identified patent and that said Letters Patent is hereby corrected as shown below:

Column 3, line 49: Change "if" to read --is--.

Claim 12, lines 2 and 3: change "either claim 11" to read:

-- claim 11 --.

Signed and Sealed this

Fourth Day of February 1986

[SEAL]

Attest:

DONALD J. QUIGG

Attesting Officer

Commissioner of Patents and Trademarks